United States Patent
Quandt et al.

(10) Patent No.: US 8,308,928 B2
(45) Date of Patent: Nov. 13, 2012

(54) THROMBOSIS FILTER WITH COVER LAYER

(75) Inventors: Eckhard Quandt, Heikendorf (DE); Christiane Zamponi, Kiel (DE); Clemens Schmutz, Köln (DE)

(73) Assignee: Acandis GmbH & Co. KG, Pfinztal (DE)

( * ) Notice: Subject to any disclaimer, the term of this patent is extended or adjusted under 35 U.S.C. 154(b) by 699 days.

(21) Appl. No.: 12/438,635

(22) PCT Filed: Aug. 24, 2007

(86) PCT No.: PCT/EP2007/007455
§ 371 (c)(1),
(2), (4) Date: Oct. 15, 2009

(87) PCT Pub. No.: WO2008/022799
PCT Pub. Date: Feb. 28, 2008

(65) Prior Publication Data
US 2010/0145380 A1    Jun. 10, 2010

(30) Foreign Application Priority Data
Aug. 25, 2006   (DE) .......................... 10 2006 039 840

(51) Int. Cl.
C25D 1/00       (2006.01)
A61L 33/00      (2006.01)
B29C 37/02      (2006.01)
(52) U.S. Cl. ............ 205/67; 205/223; 427/2.1; 264/138
(58) Field of Classification Search ................... 427/2.1; 264/138; 205/67, 122, 223
See application file for complete search history.

(56) References Cited

U.S. PATENT DOCUMENTS
2006/0241677 A1 * 10/2006 Johnson et al. ............... 606/200
2007/0178221 A1 *  8/2007 Sims et al. ................... 427/2.21

FOREIGN PATENT DOCUMENTS
WO    0004204 A1    1/2000
WO    0110342 A1    2/2001
WO    0187371 A2   11/2001
WO 2004008504 A1    1/2004

OTHER PUBLICATIONS

Buchaillot, L., et al.: Thin film of titanium/nickel shape memory alloy for multi-degree of freedom microactuators, Seisan Kenkyu, Tokyo Daigaku Seisangijutsu Kenkyujo, Tokyo, JP, pp. 22-23, XP009087245, Jan. 1, 1999.
Rumpf, H., et al.: Near Net-Shape Fabrication of Superelastic NiTi Devices by Sputtering and Photoetching, Materials Transactions, vol. 47, No. 3, pp. 523-526, 2006.

* cited by examiner

*Primary Examiner* — Luan Van
(74) *Attorney, Agent, or Firm* — Panitch Schwarze Belisario & Nadel LLP

(57) ABSTRACT

A method is provided for applying a cover layer (9) to a net structure (4) to be used for medical purposes, in particular a thrombosis filter. The net structure (4) is applied to a planar substrate (1) that covers openings (5) of the net structure on one side, wherein the openings (5) across the uncovered side are filled with a sacrificial material (7), in particular copper. The net structure (4) is lifted from the substrate (1). A cover layer (9) is deposited on the surface previously covered by the substrate, and the sacrificial material (7) is removed.

14 Claims, 2 Drawing Sheets

THROMBOSIS FILTER WITH COVER LAYER

CROSS-REFERENCE TO RELATED APPLICATIONS

This application is a Section 371 of International Application No. PCT/EP2007/007455, filed Aug. 24, 2007, which was published in the German language on Feb. 28, 2008, under International Publication No. WO 2008/022799 A2 and the disclosure of which is incorporated herein by reference.

BACKGROUND OF THE INVENTION

The present invention relates to a method for applying a cover layer to a net structure to be used for medical purposes, in particular a thrombosis filter. The invention also relates to a thrombosis filter provided with a cover layer according to this method.

Net structures of this kind can have different applications in medicinal treatments. They can, for example, be used as vessel supports, in particular as stents. In addition to their use as permanent implants, the net structures according to the invention can be used as thrombosis filters, for example during vessel widening (angioplasty) via a cardiac catheter. Finally, the risk of a thrombus forming cannot be excluded in the case of interventions in the blood vessels despite the use of state-of-the-art medical engineering. The known thrombosis filters are placed in folded-together condition in the desired place in the vein, in particular in the flow direction of the blood circulation behind the constriction (stenosis). When opened up it lies on the internal vessel wall before the performance of a balloon angioplasty.

In the case of a balloon angioplasty of this kind, a balloon catheter is inserted from the groin via a guide wire into the stenosis and inflated. The expanded cross section achieved thereby is generally maintained by an implanted stent. It is precisely with an intervention of this kind that there is a risk of thrombotic material dropping off the vessel walls and being transported via the blood stream into narrower vessels. Here, the material can cause a thrombosis or even an embolism, wherein a pulmonary embolism or a stroke can represent a life-threatening emergency. The net structure of the thrombosis filter can then enable any resulting thrombus to be filtered out and removed together with the thrombosis filter. Thrombosis filters of this kind are known, for example, from European Patents EP 1 207 810 B1 and EP 619 720 B1.

BRIEF SUMMARY OF THE INVENTION

It is the object of the invention to improve a net structure of this kind to be used for medical purposes with measures that can be described simply to the extent that, in therapeutic use, the surrounding tissue is better protected and that a filter function optimized to match the application in question is possible. It is in particular the object of the invention to provide an easy-to-implement method for the production of a cover layer on a net structure of this kind. It is also an object of the invention to develop a covered net structure of this kind which is more efficiently able to filter out a thrombus with more cost-efficient production and simple handling.

The essential fundamental idea of the invention is to use an existing net structure, for example a commercially available thrombosis filter, and to cover openings in its surface with a cover layer. According to an embodiment of the invention, this is achieved by first filling up the openings to be covered with a sacrificial material so that a continuous surface is formed. Following this, covering material is deposited thereupon, before the sacrificial material is subsequently removed. What remains is the covering material, which has sufficient hold on the surface formed by the net structure. To summarize, this process comprises the following steps:

Firstly, the net structure is applied to a planar substrate that covers openings of the net structure on one side. The substrate is adapted in accordance with the surface of the net structure, wherein in the simplest case a level and as-smooth-as-possible substrate is selected. The substrate and net structure must lie on each other in such a way that the openings of the net structure are tightly closed to a certain extent. The openings can then be filled across the uncovered side with a removable sacrificial material, in particular with copper. The "filled" net structure is then separated from the substrate and has, on the side facing the substrate, a relatively smooth enclosed surface on which the cover layer is deposited. Finally, when the sacrificial material is removed, the net structure covered by the cover layer remains. The cover layer can then be modified in the following steps, for example with larger or smaller pores.

In this way, net structures covered by a cover layer can be produced simply and cost effectively. The cover layer is hereby firmly bonded to the net structure, which means its surface is accessible for further processing without having to fear the dissolution of the bond to the net structure. Such processing can be the introduction of pores the size of which enable the fineness of the thrombosis filter to be set as desired. Naturally, the method according to the invention is also suitable for covering not the entire net structure, but only certain partial regions. This flexibility facilitates a plurality of possible adaptations to different conditions of use, in particular, it enables the opening size and shape and the surface structure of thrombosis filter to be designed as desired.

To achieve a good bond between the net structure and the cover layer, it can be advantageous if the material of the net structure is used for the deposition of the cover layer. Due to its special biocompatibility and also due to its shape memory, net structures are often produced from NiTi alloys, so Nitinol is suitable for producing the cover layer.

Since, the structures of relevance here involve relatively small components in the centimeter range with only low thicknesses of a few tenths of a micrometer, and the layers are correspondingly thin, the application of the layers is advantageously performed using methods such as vapor deposition or sputtering and galvanic methods. Ideally, the sacrificial layer is deposited galvanically. A preferred embodiment of the invention therefore comprises using a conductive substrate or providing a non-conductive substrate with an electrode layer, in particular a gold layer, which is applied to the net structure. The gold layer serves as a so-called "starting layer" for the electroplating. A suitable substrate is a silicon (Si) wafer. The substrate provided with the electrode layer is not subject to material wear and, following separation from the net structure, can be re-used or recycled, which also reduces the costs.

It is advantageous to ensure there is a firm bond between the substrate and the net structure which can be provided, for example, by an adhesive bond. However, here care should be taken to ensure that the adhesive does not function as an insulating layer in front of the openings. It is therefore of advantage to use a light-sensitive varnish as the adhesive on the net structure. This enables the light-sensitive varnish serving as an adhesive to be exposed to light from the uncovered side and the places exposed to light to be removed in a rinsing step. A varnish of this kind guarantees precise adhesion of the net structure and is simultaneously able to protect the net structure in the subsequent etching steps. In the region of the openings of the net structure, after exposure to light, the varnish can be removed free of residue from the substrate, in particular from the gold layer so that before the filling with the sacrificial material no reworking is necessary. With this lithographic step, it is also possible, if required, to apply a lithographic structuring to the varnish by masking.

As described above, the deposition of the metallic sacrificial material, in particular of the copper, in a galvanic method is an essential component of the method according to the invention. Here, the net structure bonded to the Si wafer is galvanically coated with the metal in a bath. The process is stopped when the openings of the net structure are filled up with the deposited layer. In a preferred embodiment, sacrificial material is deposited until the openings are filled up to over the edge and the sacrificial material forms a coherent surface. This simplifies the further handling, since, irrespective of its adhesion to the net structure, the coherent sacrificial material is not able to fall out of the individual openings thereof.

After the galvanic growth of the sacrificial material, the substrate is removed. In the case of a Si wafer, this can be performed mechanically or by dissolving the wafer, for example in potassium hydroxide. Otherwise, the removal is performed by an etching step on the material to be dissolved. Similarly, the electrode layer can also be etched away. The varnish protecting the net structure varnish can be removed with acetone. Au, Cr, FeCo or the like can also be selected as the sacrificial material. It is advantageous if the electrode layer and the galvanically deposited layer can be etched selectively one under the other and against the material of the net structure.

In a further preferred embodiment, a film made of metal, in particular a nickel-titanium (NiTi) alloy, for example Nitinol, is applied, in particular vapor-deposited or sputtered, as the cover layer. The use of NiTi, in particular Nitinol, is known from the production of stents. The super-elastic properties of NiTi are of particular advantage with devices for use in the medical field, which are exposed to extreme deformation in the body during use. In addition, biocompatibility is a further essential feature of these alloys. Therefore, a NiTi alloy is particularly preferred for the covering of the net structure of a thrombosis filter, in particular since NiTi is a preferred representative of the shape memory alloys, since it is at least 8% pseudoelastically deformable, corrosion-resistant and high-strength.

The thin cover layer is advantageously produced using a physical deposition method, preferably by cathode sputtering. Thereby, sputtered NiTi films of this kind display super-elastic behavior at body temperature with an elongation of more than 6.5% with a plateau tension of 400 MPa. After the application of the NiTi-layer, the copper can be removed from the thrombosis filter by etching.

This produces a particularly preferred embodiment of the invention with the application of the covering layer to a net structure in a combination of photolithography, electroplating and sputter technology.

To produce a thrombosis filter, which must have, on the one hand, a certain permeability and, on the other hand, sufficient retaining power, including for smaller thrombi, the cover layer, in particular in a photolithographic step, is structured by the introduction of a plurality of larger or smaller pores. The number and the size of the pores, which can have any cross section, determine the filter functionality.

Therefore, a further essential fundamental idea of the invention comprises the suggestion of a thrombosis filter with a net-type structure formed from wire for placing in a blood vessel lumen with planar cover layer applied by a deposition method on one side of the net-type structure which at least partially covers the openings of the net-type structure. A thrombosis filter embodied in this way can be produced simply and on a large scale with its net-type structure and only then optimized for the respective field of application with a suitably structured cover layer. The combination of net structures, created for example by laser cutting, and the subsequent application of a thin metallic layer, which can be then be structured, has advantages from the point of view of production technology. Despite the simple production of the net structure, the ability of the cover layer to be structured means the advantages of finer filters and tissue-protecting surfaces are retained.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1A:
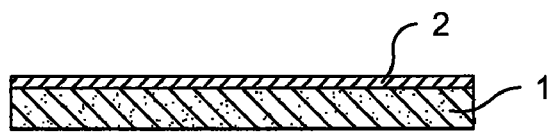
FIGS. 1a through 1i are schematic diagrams showing the steps for covering a net-type structure according to an embodiment of the method of the invention.
Figure 1B:
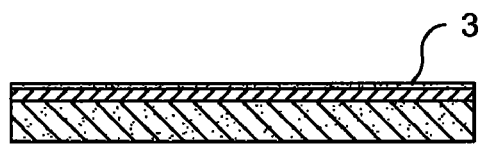
Figure 1C:
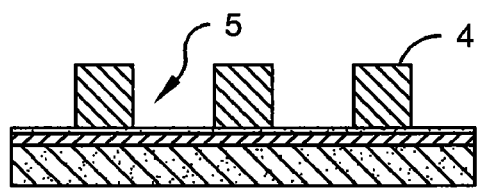
Figure 1D:
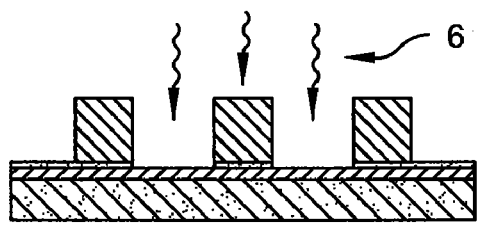

FIG. 1a is a schematic view of a section through a substrate 1, which is here formed from an Si wafer. This is coated by an electrode layer 2 a few μm thick made of gold. In a following step, shown in FIG. 1b, the gold layer is provided with a layer 3 made of photoresist, which serves as a bonding layer. In FIG. 1c the net structure 4 as the framework of the thrombosis filter is stuck on the adhesive varnish layer 3, wherein the net structure 4 comprises a plurality of openings 5. In the step in FIG. 1d the varnish layer 3 is exposed to light 6 in the region of the openings 5, whereby the region of the varnish layer 3 exposed to light is removed following the development of the gold layer 2.

Figure 1E:
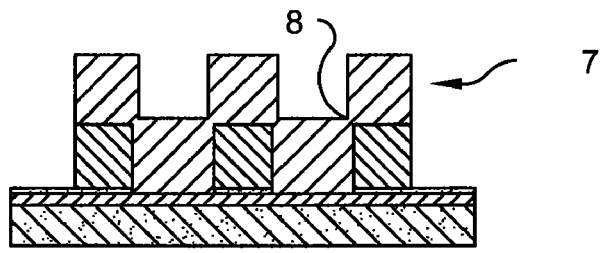
Figure 1F:
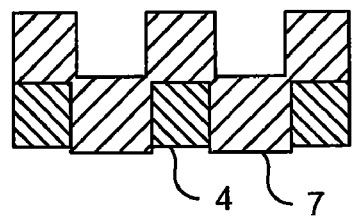
Figure 1G:
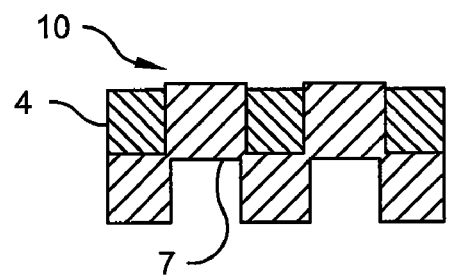
Figure 1H:
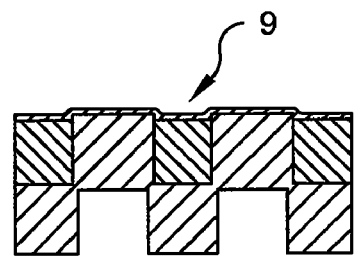
Figure 1I:
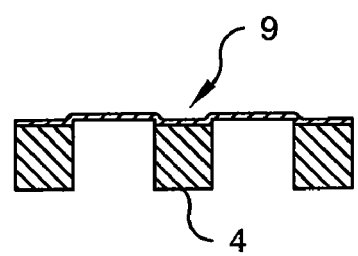

Now, a sacrificial material, here copper 7, is deposited on the gold layer 2 and the net structure 4 in a galvanic process. The deposition is performed until the copper 7 fills up the openings 5 and in the transitional region 8 has a bond with the copper 7 deposited on the net structure 4 (FIG. 1e). In the next step (FIG. 1f, the Si wafer 1 with the gold layer 2 and the remaining varnish layer 3 are removed from the net structure 4 filled up with the copper 7. Then, the net structure 4, together with the sacrificial material 7, is rotated (FIG. 1g), and with sputtering technology a metallic layer, here a thin NiTi cover layer 9, is deposited on the structured surface 10 formed from the net structure 4 and the copper 7 (FIG. 1h). In this case, the NiTi-cover layer 9 bonds to the structured surface 10. Finally, the sacrificial material 7 on the net structure 4 and in the openings 5 thereof is removed by a selective etching medium, e.g., 40% $HNO_3$, $Fe_3Cl$ or ammonium peroxodisulfate solution so that only the net structure 4 provided with a cover layer 9 remains (FIG. 1i). The cover layer 9 can now be provided with pores (not shown). This can be performed with a common photolithographic and wet-chemical etching method, for example using a photoresist and a selective etching agent.

In this way, it is possible to coat medical NiTi thrombosis filters with a permeable NiTi covering having a thickness of 0.1 to 100 μm, wherein a preferred layer thickness is approximately 3 μm.

Figure 2:
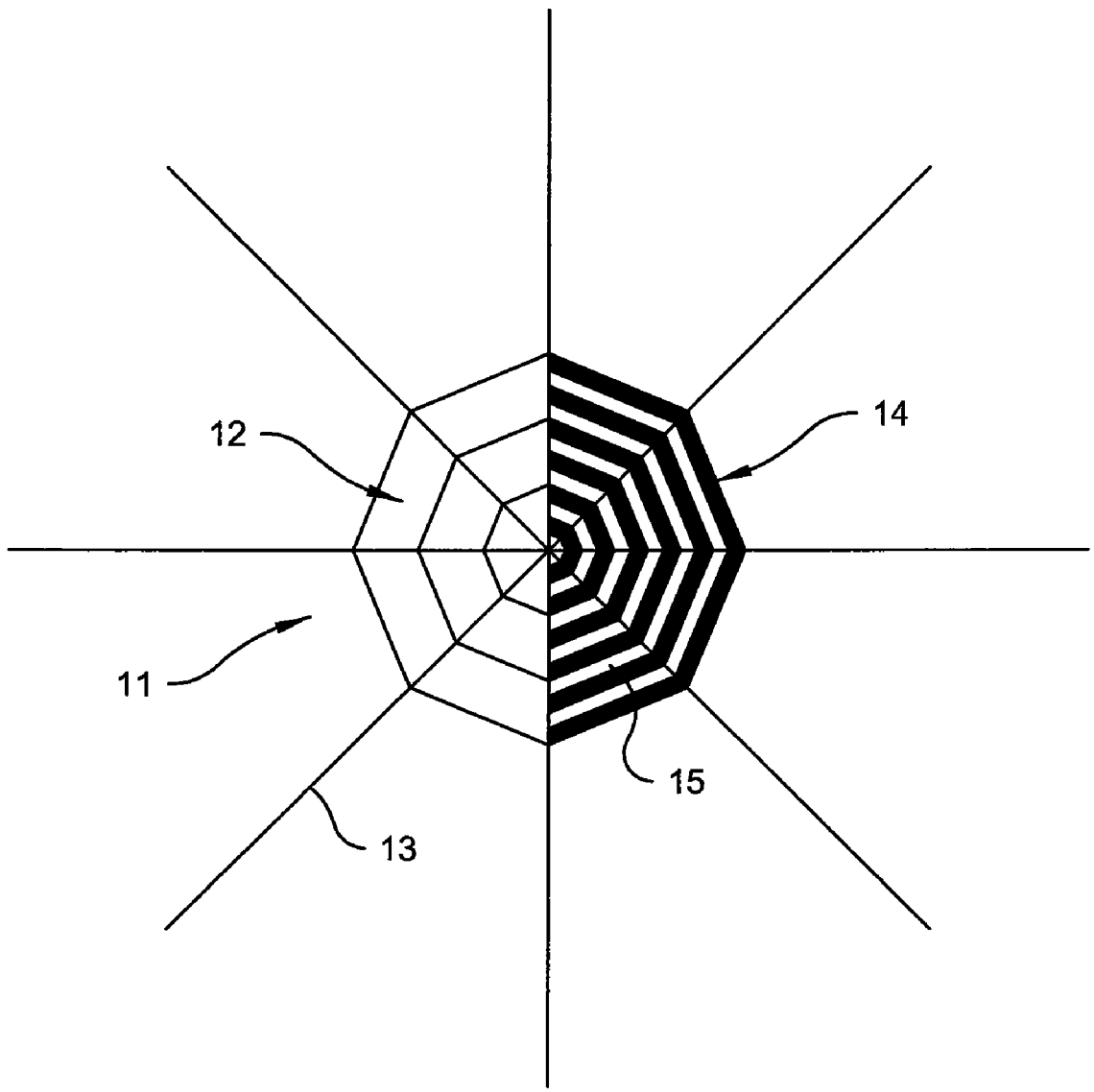
FIG. 2 is a schematic plan view of a net-type structure half with and half without a cover layer according to an embodiment of the invention.

The left side of FIG. 2 shows an uncovered net structure 11 having an internal region 12 from which individual wires 13 protrude in a star shape. The diameter of the internal region 12 is matched to that of blood vessels. The individual wires 13 are positioned for introduction into the blood vessel and spread out again after positioning. When spread out, they serve to anchor the thrombosis filter in the blood vessel. To form the thrombosis filter, the open net structure 11 is coated with a cover layer 14 (right hand side of the diagram), which here is interrupted by concentric openings, which form permeable pores 15.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for applying a cover layer to a net structure to be used for medical purposes, the method comprising the steps of:
   applying the net structure to a planar substrate to cover openings of the net structure on one side,
   filling the openings across an uncovered side of the net structure with a sacrificial material,
   lifting the net structure and the sacrificial material from the substrate,
   depositing a cover layer on a surface of the net structure and the sacrificial material previously covered by the substrate, and
   removing the sacrificial material from the net structure and the cover layer.

2. The method according to claim 1, wherein the net structure is a thrombosis filter.

3. The method according to claim 1, wherein the sacrificial material comprises copper.

4. The method according to claim 1, further comprising a step of:
   covering the substrate with an electrode layer, on which the net structure is applied.

5. The method according to claim 4, wherein the electrode layer comprises a gold layer.

6. The method according to claim 4, wherein the net structure is glued to the electrode layer by a bonding layer.

7. The method according to claim 6, wherein the bonding layer comprises a light-sensitive varnish.

8. The method according to claim 7, wherein the light-sensitive varnish is exposed to light from an uncovered side of the substrate, and wherein portions of the varnish exposed to light are removed in a rinsing step.

9. The method according to claim 1, wherein the sacrificial material is deposited in a galvanic method.

10. The method according to claim 9, wherein the sacrificial material is deposited until the openings are filled to above an edge of the openings and the sacrificial material forms a coherent surface.

11. The method according to claim 1, wherein the cover layer is applied as a film comprising metal.

12. The method according to claim 11, wherein the metal comprises a NiTi alloy and is applied by vapor-deposition or sputtering.

13. The method according to claim 1, wherein the cover layer is structured by the introduction of pores.

14. The method according to claim 13, wherein the cover layer is structured in a photolithographic step.

* * * * *